United States Patent [19]

Jiang et al.

[11] Patent Number: 5,821,230
[45] Date of Patent: Oct. 13, 1998

[54] GNRH ANTAGONIST DECAPEPTIDES

[75] Inventors: Guangcheng Jiang, San Diego, Calif.;
Graeme Semple, Hamphire, United Kingdom

[73] Assignee: Ferring BV, Hoofddorp, Netherlands

[21] Appl. No.: 837,041

[22] Filed: Apr. 11, 1997

[51] Int. Cl.$^6$ .............. A61K 38/09; C07K 7/06
[52] U.S. Cl. ............................ 514/15; 530/328
[58] Field of Search ................ 514/15; 530/328

[56] References Cited

U.S. PATENT DOCUMENTS

| | | | |
|---|---|---|---|
| 4,800,191 | 1/1989 | Schally et al. | 514/15 |
| 4,866,160 | 9/1989 | Coy | 530/313 |
| 4,935,491 | 6/1990 | Folkers et al. | 530/313 |
| 5,064,939 | 11/1991 | Rivier et al. | 530/317 |
| 5,073,624 | 12/1991 | Coy | 530/313 |
| 5,171,835 | 12/1992 | Janaky et al. | 530/313 |
| 5,198,533 | 3/1993 | Schally et al. | 530/313 |
| 5,296,468 | 3/1994 | Hoeger et al. | 514/15 |
| 5,470,947 | 11/1995 | Folkers et al. | 530/313 |
| 5,506,207 | 4/1996 | Rivier et al. | 514/15 |
| 5,508,383 | 4/1996 | Sauer et al. | 530/313 |
| 5,516,887 | 5/1996 | Deghenghi et al. | 530/313 |

*Primary Examiner*—Cecilia J. Tsang
*Assistant Examiner*—Cecilia F. Wang
*Attorney, Agent, or Firm*—Fitch, Even, Tabin & Flannery

[57] ABSTRACT

Peptides are provided which have improved duration of GnRH antagonistic properties and/or which can be synthesized more economically. These antagonists may be used in the same manner as the compounds of which they are analogs to regulate fertility and to treat steroid-dependent tumors and for other short-term and long-term treatment indications. One particularly effective peptide, a decapeptide analog of the GnRH antagonist Acyline, has the formula: Ac-D-2Nal-D-4Cpa-D-Dpr(methylcarbamoyl)-Ser-4Aph(acetyl)-D-4Aph(acetyl)-Leu-Lys(isopropyl)-Pro-D-Ala-$NH_2$. It continues to exhibit very substantial suppression of LH secretion at 96 hours following injection. Other economically attractive and pharmacologically effective analogs have the formulas: Ac-D-2Nal-D-4Cpa-$Xaa_3$-Ser-4Aph(acetyl)-D-4Aph(acetyl)-Leu-Lys(isopropyl)-Pro-D-Ala-$NH_2$; and Ac-D-2Nal-D-4Cpa-$Xaa_3$-Ser-4Aph(hydroorotyl)-D-4Aph(acetyl)-Leu-Lys(isopropyl)-Pro-D-Ala-$NH_2$, wherein $Xaa_3$ is D-Gln or Gln.

20 Claims, No Drawings

GNRH ANTAGONIST DECAPEPTIDES

This invention relates generally to peptides which are antagonists of human gonadotropin releasing hormone (GnRH) and have advantageous physical, chemical and biological properties. More particularly, the present invention relates to decapeptides which inhibit the gonadal function and the release of the steroidal hormones progesterone and testosterone and which are less expensive to make than comparable GnRH peptide antagonists and to methods of administering pharmaceutical compositions containing such decapeptides for such purpose and particularly to manage conditions resulting from the hypersecretion of gonadal steroids.

BACKGROUND OF THE INVENTION

Follicle stimulating hormone (FSH) and luteinizing hormone (LH), sometimes referred to as gonadotropins or gonadotropic hormones, are released by the pituitary gland which is attached by a stalk to the region in the base of the brain known as the hypothalamus. These hormones, in combination, regulate the functioning of the gonads to produce testosterone in the testes and progesterone and estrogen in the ovaries, and they also have other biological functions.

Hormone release by the anterior lobe of the pituitary gland usually requires prior release of hormones produced by the hypothalamus. A hypothalamic hormone which triggers the release of the gonadotropic hormones, particularly LH, is generally now referred to as GnRH. GnRH was isolated and characterized as a decapeptide some 25 years ago. Shortly thereafter, it was found that analogs of GnRH having a D-isomer instead of Gly in the 6-position have greater binding affinity/strength to the receptor and greater biological potency than the native hormone; one example is [D-Ala$^6$]-GnRH (U.S. Pat. No. 4,072,668) having the following formula: pGlu-His-Trp-Ser-Tyr-D-Ala-Leu-Arg-Pro-Gly-NH$_2$.

The formula for the GnRH analog represented above is in accordance with conventional representation of peptides where the amino terminus appears to the left and the carboxyl terminus to the right. The position of each amino acid residue is identified by numbering the amino acid residues from left to right. In the case of GnRH, the hydroxyl portion of the carboxyl group of glycine at the C-terminus has been replaced with an amino group(NH$_2$) i.e. the C-terminus is amidated. The abbreviations for the individual amino acid residues above are conventional. Except for glycine, the amino acids and other modifiers attached thereto set forth hereinafter should be understood to be of the L-configuration unless noted otherwise to be the D-isomer.

The administration of GnRH analogs that are antagonistic to the normal function of GnRH has been used to suppress secretion of gonadotropins generally in mammals and to suppress or delay ovulation. Because GnRH antagonists are capable of immediate inhibition of pituitary gonadotropin secretion by competing with the stimulatory effect of endogenous GnRH, such analogs of GnRH are being investigated for their potential use as suppressives, as contraceptives and for regulating conception periods and for the control of the timing of ovulation for in vitro fertilization. For example, GnRH antagonists may be used for the treatment of precocious puberty and endometriosis and other such conditions which result from hypersecretion of gonadotropins, and they are also useful for regulating the secretion of gonadotropins in male mammals, where they can be employed to arrest spermatogenesis, e.g. as male contraceptives, for treatment of male sex offenders, and for treatment of prostatic hypertrophy. GnRH antagonists are also used to treat steroid-dependent tumors, such as prostatic and mammary tumors. In the female, they can also be used to treat hirsutism. GnRH antagonists offer advantages over the currently available, lengthy administration regimen of GnRH agonists, such as the absence of an initial gonadotropin stimulation (flare) and the dose proportional efficacy.

The development of these compounds has been hampered by histamine-release inducing properties, i.e. cause histamine to be released from mast cells which cells are found in the skin, the gingiva and other locations throughout the body. As a result, inflammation is caused, at times resulting in edema of the face and elsewhere on the skin. Certain GnRH antagonists that are effective in preventing ovulation have the undesirable adverse side effect of stimulating histamine release; thus, the design of GnRH analogs has generally been directed to providing peptides that retain the biological efficacy but do not exhibit such undesirable histamine release, see J. Rivier et al., *J. Med. Chem.*, 29, 1846–1851 (1986). The occurrence of depot formation after injection due to "gelling" results in release from the injection site that may be difficult to control, and improvements in solubility of these peptides have been sought to avoid such gelling.

The aim of GnRH antagonists is generally to suppress endogenous gonadotropins and/or sex steroids, and such suppression may be required for either short periods of time (e.g. during infertility treatment) or for long periods (e.g. during the treatment of endocrine cancers). Depending on the specific indication, short-term treatment varies from 1 day to about 6 weeks, whereas long-term treatment may last from several months to many years. The subdivision into short- and long-term treatment has a practical background. Presently available pharmaceutical formulations of GnRH antagonists permit daily subcutaneous administration only; therefore, long-acting, sustained-release formulations are required if one is to effect long-term treatment, with such formulations being only in the early stages of pharmaceutical development.

Short-term GnRH antagonist treatment is anticipated to be effective in the following situations:
(1) diagnostic;
(2) prevention of luteinizing hormone (LH) surges in controlled ovarian hyperstimulation (COH) for assisted reproductive techniques;
(3) suppression of increased LH levels during induction of ovulation in polycystic ovarian disease (PCOD) to decrease the incidence of spontaneous abortion;
(4) premenstrual syndrome (PMS);
(5) treatment of threatening ovarian hyperstimulation syndrome (OHSS);
(6) preparation for surgery of leiomyoma;
(7) functional menometrorrhagia;
(8) male contraception by (initiating the) suppression of gonadotropins;
(9) protection of the gonads during cytostatic treatment for cancer; and
(10) interval treatment of endometrial cancer between diagnosis and surgery.

Long-term GnRH-antagonist treatment (several months to many years) is expected to be effective treatment in the following indications;
(1) prostate cancer;
(2) breast cancer;
(3) endometrial cancer;
(4) ovarian cancer;

(5) benign prostatic hypertrophia;
(6) precocious puberty;
(7) endometriosis;
(8) hyperandrogenism; and
(9) promotion of hair growth.

Presently, the long period of treatment for these indications has been considered to require a sustained release GnRH antagonist depot preparation because daily subcutaneous injections are generally considered to be unacceptable. However, any such treatment of males should be carried out along with testosterone replacement to maintain libido. Linkage of GnRH analogs to cytotoxic radicals may increase the efficacy of cancer treatment using these compounds with a concomitant decrease of general toxicity.

The search for improved GnRH antagonists has resulted in the making of Antide, i.e. [Ac-D-2Nal$^1$, D-4ClPhe$^2$, D-3Pal$^3$, Lys(Nic)$^5$, D-Lys(Nic)$^6$, ILys$^8$, D-Ala$^{10}$]-GnRH; and Cetrorelix, i.e. [Ac-D-2Nal$^1$, D-4ClPhe$^2$, D-3Pal$^3$, D-Cit$^6$, D-Ala$^{10}$]-GnRH. U.S. Pat. No. 5,516,887 describes GnRH antagonists which are said to be more effective than Antide in suppressing plasma testosterone, e.g.[Ac-D-2Nal$^1$, D-4ClPhe$^2$, D-3Pal$^3$, D-N$^\epsilon$-carbamoyl Lys$^6$, Ilys$^8$, D-Ala$^{10}$] -GnRH, which is referred to as Antarelix.

U.S. Pat. No. 5,296,468, issued Mar. 22, 1994, discloses the design and synthesis of a number of GnRH antagonists wherein the side chains of selected residues are reacted to create cyanoguanidino moieties, some of which subsequently spontaneously convert to a desired heterocycle, e.g. a 3-amino-1,2,4-triazole(atz). Such cyanoguanidino moieties are built upon the omega-amino group in an amino acid side chain, such as lysine, ornithine, 4-amino phenylalanine (4Aph) or an extended chain version thereof, such as 4-amino homophenylalanine (4Ahp). GnRH antagonists having such significantly modified or unnatural amino acids in the 5- and 6-positions exhibit good biological potency, and those built upon 4Aph are generally considered to be preferred. One that is especially preferred is Azaline B, i.e. [Ac-D-2Nal$^1$, D-4ClPhe$^2$, D-3Pal$^3$, 4Aph(atz)$^5$, D-4Aph (atz)$^6$, ILys$^8$, D-Ala$^{10}$]-GnRH. U.S. Pat. No. 5,506,207 discloses biopotent GnRH antagonists wherein amino-substituted phenylalanine side chains of residues in the 5- and 6-positions are acylated; one particularly potent decapeptide is Acyline, i.e. [Ac-D-2Nal$^2$, D-4ClPhe$^2$, D-3Pal$^3$, 4Aph(Ac)$^5$, D-4Aph(Ac)$^6$, ILys$^8$, D-Ala$^{10}$]-GnRH.

Despite the attractive properties of these GnRH antagonists, the search has continued for still further improved GnRH antagonists, particularly those which exhibit long duration of biological action and which can be formulated less expensively. It can frequently be important that a peptide analog, for both short-term and long-term treatment indications, should exhibit a long duration of activity with respect to LH secretion, a property which may be enhanced by the peptide's resistance to proteolytic enzyme degradation in the body, and to be relatively low in histamine release. In addition, to facilitate administration of these compounds to mammals, particularly humans, without significant gelling, it is considered extremely advantageous for such GnRH antagonistic decapeptides to have high solubility in water at normal physiologic pH, i.e. about pH 5 to about pH 7.4. Moreover, as these compounds begin to anticipate entering the clinical stage, the cost of preparation becomes a factor, and it is noticed that all of the above peptides utilize D-3Pal in the 3-position—a particularly expensive protected amino acid to purchase or synthesize. Relatively equally biopotent analogs that can be less expensively synthesized would be attractive, and the 3-position is one target for cost reduction.

SUMMARY OF THE INVENTION

It has now been found that, by the substitution in the 3-position of less expensive residues, the cost can be reduced without reducing biopotency or this subclass of GnRH antagonists which includes Cetrorelix, Antarelix, Acyline, Azaline B, Antide and others. Not only are these analogs less expensive to synthesize than peptides containing the heretofore preferred D-3Pal$^3$, but also the particularly advantageous property of long duration of bioactivity is often unexpectedly obtained. Generally, GnRH antagonist decapeptides having the following formula, and the pharmaceutically acceptable salts thereof and closely related analogs, are less expensive to synthesize than comparable prior art compounds and often have improved pharmacological properties, particularly long duration of bioactivity:

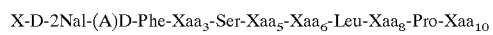

wherein:

X is an acyl group of 7 carbon atoms or less or Q, with Q being

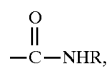

with R being H or lower alkyl;

A is 4Cl, 4F, 4Br, 4NO$_2$, 4CH$_3$, 4OCH$_3$, 3,4Cl$_2$ or C$^\alpha$Me4Cl;

Xaa$_3$ is D-Gln, Gln, D-Asn, Asn or D-Dpr(Q);

Xaa$_5$ is Tyr, 4Aph(Q$_1$), 4Amf(Q$_1$), 4Ahp(Q$_1$) or Lys(Nic), with Q$_1$ being Q, For, Ac, 3-amino-1,2,4-triazole, β-Ala(3-amino-1,2,4-triazole), Gab(3-amino-1,2,4-triazole) D/L-Hor or D/L-Imz;

Xaa$_6$ is D-4Aph(Q$_2$), D-4Amf(Q$_2$), D-4Ahp(Q$_2$), D-Lys (Nic), D-Cit, D-Hci or D-3Pal, with Q$_2$ being Q, For, Ac, 3-amino-1,2,4-triazole, β-Ala(3-amino-1,2,4-triazole), Gab(3-amino-1,2,4-triazole))D/L-Hor or D/L-Imz;

Xaa$_8$ is Lys(ipr), Arg, Har, Har(Et$_2$), or Arg(Et$_2$); and

Xaa$_{10}$ is D-Ala-NH$_2$, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$.

These antagonists are particularly useful to suppress the secretion of gonadotropins and as fertility regulators in humans because they exhibit long duration of activity as a result of the residue that is present in the 3-position of the decapeptide. They have excellent solubility in aqueous buffers at physiologic pHs and acceptable side effects with respect to stimulation of histamine release, i.e. better than the GnRH superagonists which are now being clinically used; they also exhibit minimal gelling upon subcutaneous (sc) injection. These GnRH antagonists also perform well in an anaphylactoid assay causing a relatively small wheal. As a result, these peptides find particular use in administration to mammals, especially humans, as fertility regulators and for the treatment of pathological conditions such as precocious puberty, hormone-dependent neoplasia, dysmenorrhea, endometriosis, steroid-dependent tumors, and the other short-term and long-term indications mentioned hereinbefore. They are also useful diagnostically.

Because these GnRH antagonists are readily soluble in the physiologic pH range of about 5 to about 7.4, they can be formulated and administered in concentrated form, particularly at a pH between about 5 and about 7. Because of their polar character, they are particularly suitable for use in slow-release preparations based upon known copolymers. Because of the 3-position substitutions, these analogs are less expensive to produce than comparable analogs containing D-3Pal[3]. Because many of these GnRH antagonists exhibit effective suppression of LH and FSH for long duration, they are particularly effective for the contraceptive treatment of male mammals (with the administration of testosterone) and for the treatment of steroid-dependent tumors.

DETAILED DESCRIPTION OF THE PREFERRED EMBODIMENTS

Over the last 10–12 years, the particular properties of each of the 10 residues in the sequence of GnRH, from the standpoint of creating effective antagonists, have been studied in depth, and as a result of these studies, it has been discovered that there are various equivalent residues that can be chosen and that substitutions of one of these equivalents for another does not significantly detract from the biological potency of decapeptide GnRH antagonists. Such equivalent substitutions may be made in the GnRH antagonists of the present invention.

For example, it has become generally accepted that the inclusion of a para-substituted D-Phe or 2,4dichloro-substituted D-Phe or D-C$^\alpha$methyl4ClPhe residue in the 2-position adds significantly to GnRH antagonist activity; however, the specific identity of the ring substituent is of only relatively minor importance when selected from among the following: chloro, fluoro, bromo, nitro, methyl and alkoxy. Therefore, such residues in the 2-position are considered to be the equivalent of D-4ClPhe which is commonly used therein. The N-terminus is preferably N-acylated, preferably by acetyl (Ac), but also by other acyl groups having not more than 7 carbon atoms, e.g. formyl (For), acrylyl(Acr), propionyl(Pn), butyryl(Bt), valeryl(Vl), vinylacetyl(Vac) and benzoyl(Bz); alternatively, a substituted or unsubstituted carbamoyl group may be present. Other longer acyl groups are considered to be equivalents but are less preferred. The $\alpha$-amino group on the 5-position residue may be optionally methylated, as disclosed in U.S. Pat. No. 5,110,904, to increase solubility in water, but such modification may result in a shortening of duration of LH suppression and in greater potential for histamine release. The C-terminus is preferably D-Ala-NH$_2$; however, Gly-NH$_2$, NHCH$_2$CH$_3$, AzaGly-NH$_2$, Agl-NH$_2$, D-Agl-NH$_2$, Agl(Me)-NH$_2$ and D-Agl(Me)-NH$_2$ may instead be used as they are considered to be known equivalents.

As hereinbefore disclosed, the present invention is considered to provide a genus of GnRH antagonists which are generally improvements of known GnRH antagonists that have a substitution in the 3-position and which are represented by the following formula:

X-D-2Nal-(A)D-Phe-Xaa$_3$-Ser-Xaa$_5$-Xaa$_6$-Leu-Xaa$_8$-Pro-Xaa$_{10}$ wherein:
X is an acyl group of 7 carbon atoms or less or Q, with Q being

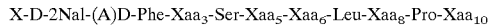

with R being H or lower alkyl;
A is 4Cl, 4F, 4Br, 4NO$_2$, 4CH$_3$, 4OCH$_3$, 3,4Cl$_2$ or C$^\alpha$Me4Cl;
Xaa$_3$ is D-Gln, Gln, D-Asn, Asn or D-Dpr(Q);

Xaa$_5$ is Tyr, 4Aph(Q$_1$), 4Amf(Q$_1$), 4Ahp(Q$_1$) or Lys(Nic), with Q$_1$ being Q, For, Ac, 3-amino-1,2,4-triazole, $\beta$-Ala(3-amino-1,2,4-triazole) or Gab(3-amino-1,2,4-triazole);

Xaa$_6$ is D-4Aph(Q$_2$), D-4Amf(Q$_2$), D-4Ahp(Q$_2$), D-Lys (Nic), D-Cit, D-Hci or D-3Pal, with Q$_2$ being Q, For, Ac, 3-amino-1,2,4-triazole, $\beta$-Ala(3-amino-1,2,4-triazole) or Gab(3-amino-1,2,4-triazole);

Xaa$_8$ is Lys(ipr), Arg, Har, Har(Et$_2$) or Arg(Et$_2$); and

Xaa$_{10}$ is D-Ala-NH$_2$, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$.

By D-Nal is meant the D-isomer of alanine which is substituted by naphthyl on the $\beta$-carbon atom, i.e., also referred to as 3-D-Nal. Preferably D-2Nal is employed wherein the attachment to naphthalene is at the 2-position on the ring structure; however, D-1Nal may also be used. D-Cpa represents chloro-D-Phe, and D-4ClPhe, i.e. D-4Cpa, is preferred. D-3Pal represents the D-isomer of alanine which is substituted by pyridyl on the $\beta$-carbon atom, with the linkage being to the 3-position on the pyridine ring, i.e. $\beta$-3-pyridyl-D-Ala. By 4Aph is meant 4NH$_2$Phe wherein the amino substituent on the phenyl ring is at the 4-position; 4NH$_2$-homophenylalanine (4Ahp) is considered its equivalent. By 4Amf is meant phenylalanine where an amino group is coupled to the 4 position on the phenyl ring through a methylene linkage. By Gab is meant gamma amino butyric acid. By atz is meant 3-amino-1,2,4-triazole. 4Aph(atz) is also known by the more precise chemical name 4-(3'-amino-1H-1',2',4'-triazoyl-5'-yl) aminophenylalanine. By Lys(Nic) is meant N$^\epsilon$-nicotinoyl lysine, i.e. the $\epsilon$-amino group of Lys is acylated with 3-carboxypyridine. By Har is meant homoarginine. By D-Cit is meant the D-isomer of citrulline, and by D-Hci is meant the D-isomer of homocitrulline, which may also be called D-N$^\epsilon$-carbamoyl lysine. By ILys or Lys(ipr) is meant N$^\epsilon$-isopropyl lysine, i.e. the $\epsilon$-amino group of Lys is alkylated. By AzaGly-NH$_2$ is meant NHNH-CONH$_2$. By Dbu is meant alpha, gamma-diamino butyric acid, and by Dpr is meant $\alpha,\beta$-diamino propionic acid. By Agl is meant $\alpha$-aminoglycine, and in Agl(Me), the side chain amino group is methylated. By Cbm is meant carbamoyl, and by MeCbm is meant methylcarbamoyl or —CONHCH$_3$. By lower alkyl is meant C$_1$–C$_5$, preferably C$_1$ to C$_3$ and more preferably C$_1$ or C$_2$, i.e. methyl(Me) or ethyl(Et).

Although the preferred D-isomers for incorporation in the 6-position of these GnRH antagonists are specifically disclosed, it should be understood that as a result of the extensive research in the field over the past two decades, there are many known equivalent D-isomers. Such prior art D-isomer substitutions may be compatible and not detract from the biopotency of these improved compounds, particularly the extended duration afforded by the 3-position substitutions disclosed herein; thus, they may optionally be utilized. Likewise, it is known that Leu[7] may be substituted by Phe[7] to provide GnRH antagonists with equivalent properties.

A preferred subgenus of GnRH antagonists has the formula:

X-D-2Nal-D-4ClPhe-Xaa$_3$-Ser-Xaa$_5$-Xaa$_6$-Leu-Lys(ipr)-Pro-D-Ala-NH$_2$ wherein:
X is an acyl group of 7 carbon atoms or less or Q, with Q being

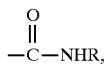

with R being H or methyl or ethyl;
Xaa$_3$ is D-Gln, Gln or D-Dpr(Q);
Xaa$_5$ is 4Aph(Ac), 4Aph(Q), 4Amf(Q), or 4Aph(atz); and
Xaa$_6$ is D-4Aph(Ac), D-4Amf(Q), D-4Aph(Q) or D-4Aph(atz).

An additional genus of GnRH antagonists embodying features of the present invention and including additional substitutions in the 5- and 6-positions has the formula:

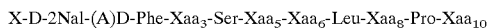

wherein:
X is For, Ac, Acr, Pn, Bt, Vl, Vac, Bz or Q, with Q being

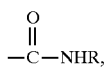

and
with R being H or lower alkyl;
A is 4Cl, 4F, 4Br, 4NO$_2$ 4CH$_3$, 4OCH$_3$, 3,4Cl$_2$ or C$^\alpha$Me4Cl;
Xaa$_3$ is D-Gln, Gln, D-Asn, Asn or D-Dpr(Q);
Xaa$_5$ is 4Aph(Q$_1$), Ahp(Q$_1$) or 4Amf(Q$_1$) with Q$_1$ being Ac, 3-amino-1,2,4-triazole, Q or

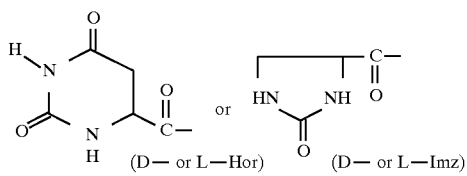

Xaa$_6$ is D-4Aph(Q$_2$), D-4Amf(Q$_2$), D-Lys(Nic), D-Cit, D-Hci or D-3Pal, with Q$_2$ being For or Q$_1$;
Xaa$_8$ is Lys(ipr), Arg, Har, Har(Et$_2$) or Arg(Et$_2$); and
Xaa$_{10}$ is D-Ala-NH$_2$, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$.

By Hor is meant the L-isomer of hydroorotic acid. By Imz is meant L-2-Imidazolidone-4-carboxylic acid. Both Hor and Imz can be used as the L- or D-isomers or a D/L mixture.

A preferred subgenus of such GnRH antagonists has the formula:

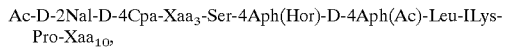

wherein
Xaa$_3$ is D-Gln, Gln or D-Dpr(Q),
with Q being

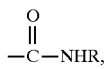

and with R being H or methyl; and
Xaa$_{10}$ is D-Ala-NH$_2$ or an equivalent.

The compounds of the present invention can be synthesized by classical peptide solution synthesis, and such synthesis is preferred for large quantities of product. To obtain limited quantities, e.g. less than 1 kg, it may be preferable to synthesize them using a solid phase technique. A chloromethylated resin or a hydroxymethylated resin may be used; however, a methylbenzhydrylamine(MBHA) resin, a benzhydrylamine (BHA) resin or some other suitable resin known in the art which directly provides a C-terminal amide upon cleavage is preferably employed. Should equivalent peptides having a substituted amide at the C-terminus be desired, they are preferably synthesized using an N-alkylamino methyl resin as taught in U.S. Pat. No. 4,569,967, issued Feb. 11, 1986. Solid phase, chain elongation synthesis is usually conducted in a manner to stepwise add individual amino acids to the chain, e.g. in the manner set forth in detail in the U.S. Pat. No. 5,296,468. Side-chain protecting groups, as are well known in the art, are preferably included as a part of any amino acid which has a particularly reactive or labile side chain when it is being coupled into the chain being built upon the resin. Such synthesis provides a fully protected intermediate peptidoresin.

One example of a chemical intermediate which might be used to synthesize a GnRH antagonist having a desired carbamoyl-containing residue in the 3-position is represented by the formula: $X^1$-D-2Nal-D-4ClPhe-Xaa$_3$ ($X^3$ or $X^5$)-Ser($X^2$)-4Aph($X^3$)-D-4Aph($X^3$)-Leu-ILys($X^4$)-Pro-$X^6$ wherein $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1) acyl-type protecting groups, such as formyl(For), trifluoroacetyl, phthaloyl, p-toluenesulfonyl(Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxycarbonyl (ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc.

$X^2$ is a protecting group for the hydroxyl side chain of Ser, e.g. Ac, Bz, trityl, DCB or benzyl ether(Bzl) and is preferably Bzl.

$X^3$ is a protecting group for a side chain amino group of Dpr or the like which is not removed when the α-amino protecting group or another amino-protecting group is removed. Illustrative examples include (1) base-labile groups, such as Fmoc, or some other weak-acid stable, aromatic urethane-type protecting group; (2) thiol-labile groups, such as dithiasuccinoyl(Dts) which may be removed or cleaved by thiolysis; (3) hydrazine-labile groups, such as phthaloyl(Pht) which is cleaved by hydrazinolysis; (4) nucleophile-labile groups, such as o-nitrophenylsulfenyl (Nps) and the like which are cleaved by thioacetamide or by weak acids or their salts; (5) photo-labile groups which are cleaved by photolysis; and (6) groups selectively removable by reduction, such as Dts. Fmoc is preferred for a Boc SPPS strategy.

$X^4$ is an acid-labile protecting group for a primary or secondary amino side chain group, such as Z or 2ClZ.

$X^5$ is hydrogen or a protecting group from the amido group of Gln, such as xanthenyl (xan). However, Gln or Asn is preferably coupled without side chain protection in the presence of hydroxybenzotriazole (HOBt).

$X^6$ may be D-Ala-, Gly-, Ala-, Agl-, D-Agl-, Agl(Me)- or D-Agl(Me)-NH-[resin support], or N(Et)-[resin support]; $X^6$ may also be an amide either of Gly or of D-Ala, or a lower alkyl substituted amide attached directly to Pro, or AzaGly-$NH_2$.

The criterion for selecting side chain protecting groups $X^2$ through $X^5$ is that the protecting group should generally be stable to the reagent under the reaction conditions selected for removing the α-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. The protecting groups initially employed for the 3-position amino acids and also for the 5- and 6-position residues are preferably removed, and selective reactions are carried out prior to cleavage of the ultimate peptide from the resin, as explained hereinafter.

When the $X^6$ group is D-Ala-NH-[resin support], an amide bond connects D-Ala to a BHA resin or to a MBHA resin; this is likewise the case when Agl or D-Agl is used at the C-terminus. When $X^6$ is N(Et)-[resin support], an amide bond connects Pro to an N-alkylaminomethyl resin (NAAM).

When the N-terminus is to be acetylated, for example, it is possible to employ acetyl as the $X^1$ protecting group for the α-amino group of β-D-Nal in the 1-position by adding it to the amino acid before it is coupled to the peptide chain; however, a reaction is preferably carried out with the peptide intermediate on the resin. After deblocking the α-amino group and while desired side chain groups remain protected, acetylation is preferably carried out by reacting with acetic anhydride, alternatively reaction can be carried out with acetic acid, in the presence of diisopropyl or dicyclohexyl carbodiimide (DIC or DCC), or by some other suitable acylation reaction as known in the art. A similar procedure is carried out when a carbamoyl or substituted carbamoyl group is desired at the N-terminus. When the deprotected side chain amino groups are modified while the residue is part of the peptide chain, the reaction may be carried out using an appropriate isocyanate in the presence of an appropriate base, for example, N,N-diisopropylethylamine (DIEA), although the use of such a base is optional. When an unsubstituted carbamoyl group is desired in the final product, the deprotected amino side chain may be reacted with benzyl isocyanate, trimethylsilyl isocyanate or tert-butyl isocyanate, with the latter being preferred. Using such a strategy, the t-butyl moiety is removed during deprotection, leaving the carbamoyl as a part of a urea group.

The invention also provides a preferred method for making a GnRH antagonist having, for example, the formula: Ac-D-2Nal-D-4Cpa-Dpr(MeCbm)-Ser-4Aph(Ac)-D-4Aph (Ac)-Leu-ILys-Pro-D-Ala-$NH_2$, which method comprises (a) forming an intermediate peptide having the formula: Boc-Ser($X^2$)-4Aph($X^3$)-D-4Aph($X^3$)-Leu-ILys($X^4$)-Pro-$X^6$ wherein $X^2$ is hydrogen or a protecting group for a hydroxyl group of Ser; $X^3$ is a base-labile, hydrazine-labile or other appropriately labile protecting group for an amino group; $X^4$ is an acid-labile protecting group for an amino side chain; $X^6$ is D-Ala-NH-[resin support]; (b) removing $X^3$ from 4Aph and D-4Aph and reacting the deprotected primary amino groups with acetic anhydride; (c) completing the chain elongation to create the intermediate $X^1$-D-2Nal-D-4Cpa-Dpr($X^3$)-Ser($X^2$)-4Aph(Ac)-D-4Aph(Ac)-Leu-ILys($X^4$)-Pro-$X^6$, wherein $X^1$ is an α-amino protecting group; (d) removing $X^3$ from 3-position residue to deprotect the side chain primary amino group of this amino acid residue of the intermediate peptide; (e) reacting this deprotected side chain primary amino group with methyl isocyanate; (f) acylating the N-terminus and (g) splitting off any remaining protecting groups and/or cleaving from resin support included in $X^6$.

Purification of the final peptide may be effected by ion exchange chromatography, partition chromatography or by using HPLC, as known in the art, see J. Rivier, et al. *J. Chromatography,* 288, 303–328 (1984) and C. Miller and J. Rivier, *BioPolymers* (Peptide Science), 40, 265–317 (1996).

The GnRH antagonists of the invention are considered to be effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. The antagonists are also effective to arrest spermatogenesis when administered to male mammals on a regular basis and can thus be used as contraceptives. Because these compounds will reduce testosterone levels and thus libido (an undesired consequence in the normal, sexually active male), it may be desirable to administer replacement dosages of testosterone along with the GnRH antagonist in order to achieve azoospermia or hair growth while maintaining libido. These antagonists can also be used to regulate the production of gonadotropins and sex steroids and for other of the long-term and short-term indications as indicated hereinbefore, and they can be used in veterinary applications as contraceptives for pets.

The peptides provided by the invention are particularly soluble at physiological pHs and can be prepared as relatively concentrated solutions for administration, particularly for subcutaneous injection. These peptides are well-tolerated in the body and do not tend to gel when administered subcutaneously at effective concentrations. Generally pharmaceutical compositions including such peptides and a suitable pharmaceutically acceptable excipient can be administered iv, ip, subcutaneously or the like at levels of between about 0.001 mg to about 2.5 mg per Kg of body weight per day, with 0.5 mg/Kg/day usually being sufficient.

The appropriately protected D- or L-hydroorotyl-containing, carbamoyl-containing and/or D- or L-Imidazolidone-carbonyl-containing amino acids are preferably synthesized and then employed in a chain elongation peptide synthesis. However, synthesis may also be effected by initially incorporating an appropriately protected 4Aph, 4Ahp, 4Amf or Dpr residue at the desired position in the peptide intermediate, and this may be the laboratory method of choice where only small quantities are initially desired. This strategy is accomplished by subsequently deprotecting the particular residue (either immediately or subsequently during the synthesis) and then reacting the deprotected side chain amino group with the desired reagent.

The present invention is further described by the examples which follow. Such examples, however, are not to be construed as limiting in any way either the spirit or the scope of the present invention. The following examples illustrate GnRH antagonists embodying various features of the invention, and all of these compounds include at least one D-isomer amino acid residue.

EXAMPLE 1

The peptide having the formula: Ac-D-2Nal-D-4Cpa-D-3Pal-Ser-Lys(Nic)-D-Lys(Nic)-Leu-ILys-Pro-D-Ala-NH$_2$ (Antide) has been found to exhibit very good biological properties as a GnRH antagonist, as has the peptide which is now referred to as Acyline and which differs from Antide in only the 5- and 6-positions. It has now been found that by substituting for the 3-position residue of these decapeptides, or other GnRH antagonists of known biopotency, a GnRH antagonist which is less expensive to make and/or which has improved duration of bioactivity in vivo can be obtained.

The following decapeptide [D-Dpr(MeCbm)$^3$]-Acyline, or alternatively, [Ac-D-2Nal$^1$, D-4Cpa$^2$, D-Dpr(MeCbm)$^3$, 4Aph(Ac)$^5$, D-4Aph(Ac)$^6$, ILys$^8$, D-Ala$^{10}$]-GnRH (Peptide No. 1) is synthesized by solid-phase synthesis. This peptide has the following formula: Ac-D-2Nal-(4Cl)D-Phe-D-Dpr(methylcarbamoyl)-Ser-4Aph (acetyl)-D-4Aph(acetyl)-Leu-Lys(isopropyl)-Pro-D-Ala-NH$_2$.

About 9.3 grams (0.54 mmol) of MBHA resin (Bachem) are initially used, and Boc-protected D-Ala is coupled to the resin over about an 8-hour period in dimethylformamide (DMF) or N-methylpyrrolidone(NMP)/CH$_2$Cl$_2$ using about 10 millimoles of Boc derivative and diisopropylcarbodiimide(DIC) and anhydrous 1-hydroxybenzotriazole (HOBt) as activating/coupling reagents. The D-Ala residue attaches to the MBHA residue by an amide bond.

Following the coupling of each amino acid residue, washing, deblocking and then coupling of the next amino acid residue are carried out in accordance with the following manual synthesis schedule for about 0.5 to 1 gram of starting resin:

| STEP | REAGENTS AND OPERATIONS | MIX TIMES MIN. |
|---|---|---|
| 1 | Methanol (MeOH) wash - 15 mi. (2 times) | 1 |
| 2 | CH$_2$Cl$_2$ wash - 30 ml. (3 times) | 1 |
| 3 | 50% TFA plus 1% m-cresol in CH$_2$Cl$_2$ - 25 ml. (2 times) | 5, 20 |
| 4 | Isopropyl alcohol wash - 20 ml. (2 times) | 1 |
| 5 | TEA 10% in CH$_2$Cl$_2$ - 20 ml. (2 times) | 2 |
| 6 | MeOH wash - 15 ml. (2 times) | 1 |
| 7 | CH$_2$Cl$_2$ wash - 20 ml. (3 times) | 1 |
| 8 | Boc-amino acid (0.5–1.0 mmole) and HOBt (0.5–1.0 mmole) in 10–20 ml. of dimethylformamide (DMF): DCM or N-methylpyrrolidone (NMP): DCM, depending upon the solubility of the particular protected amino acid, plus DIC or DCC (0.5–1.0 mmole) in CH$_2$Cl$_2$ | 1–17 hours |
| 9 | MeOH wash - 15 ml. (2 times) | 1 |
| 10 | DCM wash - 20 ml. (3 times) | 1 |

The above schedule is used for coupling of each of the amino acids of the peptide of the invention after the first amino acid has been attached. N$^\alpha$Boc protection is used for each of the amino acids coupled throughout the synthesis. N$^\alpha$Boc-β-D-2Nal is prepared by a method known in the art, e.g. as described in detail in U.S. Pat. No. 4,234,571, issued Nov. 18, 1980; it is also commercially available from SyntheTech, Oregon, U.S.A. The side chain primary amino groups of 4Aph in the 5-position and of D-4Aph in the 6-position are protected by Fmoc. Benzyl ether (Bzl) is preferably used as a side chain protecting group for the hydroxyl group of Ser; however, Ser may be coupled without side chain protection. N$^\alpha$Boc-Lys(Ipr,Z) is used for the 8-position residue.

After adding Ser for the 4-position residue as N$^\alpha$Boc-Ser (Bzl), the following intermediate is present: Boc-Ser(Bzl)-4Aph(Fmoc)-D-4Aph(Fmoc)-Leu-Lys(Ipr,Z)-Pro-D-Ala-NH-[MBHA resin support]. The side chains on the amino acid residues in the 5- and 6-positions are then modified by simultaneously acetylating them after first removing the side-chain protection. The Fmoc protecting group is removed from each residue by successive treatments with 25 percent piperidine in DMF(10 ml) for about 15 minutes each. After preferably washing the peptidoresin with DMF, the newly freed amino groups are treated with a large excess of acetic anhydride in DMF at room temperature for 30 minutes, or until complete as checked using a ninhydrin test, to acetylate both side chains. The peptidoresin is then subjected to the standard wash.

Following completion of the acetylation of the 4Aph and D-4Aph residue side chains, N$^\alpha$Boc- and Fmoc-protected D-Dpr is coupled to the chain for the residue in the 3-position. Once the residue has been coupled, the Boc protection is removed, and the final two residues are subsequently added to complete the chain. After deblocking the α-amino group at the N-terminus using trifluoroacetic acid (TFA), acetylation is achieved using a large excess of acetic anhydride in dichloromethane (DCM) or DMF for about 30 minutes. By starting with an appropriately large amount of resin, portions of the peptidoresin intermediate may be removed at this time for use in 3 parallel syntheses described hereinafter.

Following acetylation of the N-terminus, about 500 mg of the peptidoresin are treated with 25% piperidine to selectively deprotect the D-Dpr side chain. It is then reacted with methyl isocyanate in the presence of 2.7 mmol of DIEA, an appropriate base, in 10 ml of DMF for 2 hours at room temperature to form the methylcarbamoyl-substituted residue.

The peptidoresin is dried, and then cleavage of the peptide from the resin and deprotection of the Ser and the Lys side chains are carried out at about 0° C. with 15 ml of HF for about 1.5 hours. Anisole (0.5 ml) is added as a scavenger prior to HF treatment. After the removal of HF under vacuum, the resin is washed twice with 100 ml of ethyl ether. The cleaved peptide is extracted with 0.2% TFA in 25% CH$_3$CN/H$_2$O, repeating the process and using 100 ml each time. The extracts are pooled and lyophilized, and they provide about 160 mg of a crude peptide powder.

Purification of the peptide is then effected by preparative high performance liquid chromatography (HPLC), as known in the art and specifically set forth in J. Rivier, et al. *J. Chromatography*, 288, 303–328 (1984). The first preparative RP-HPLC separation uses a gradient TEAP (triethylammonium phosphate) buffer system, and a final separation is carried out using a 0.1% TFA (trifluoroacetic acid) gradient, all as described in detail in the *J. Chromatography* article.

The peptide (about 51 mg) is judged to be homogeneous using capillary zone electrophoresis (CZE), and the purity is estimated to be about 100%. Amino acid analysis of the resultant, purified peptide is consistent with the formula for the prepared structure. Molecular weight as determined by liquid secondary ion mass spectrometry (LSIMS) is measured as 1527.8 Da which is in agreement with the expected mass of 1527.8 Da for this peptide.

Hydrophilicity is tested by measuring retention time using RP-HPLC with a gradient of 40% Buffer B to 70% Buffer B over 30 minutes, with Buffer A being TEAP pH 7.0 and Buffer B being 70% CH$_3$CN and 30% Buffer A at pH 7.0. Peptide No. 1 is more hydrophilic than Acyline, eluting about 1.8 minutes ahead of Acyline. Its solubility in aqueous buffers at a pH of from about 5 to about 7 and its resistance to in vivo gelling, along with long-acting biopotency to suppress circulating LH levels as described hereinafter, render it particularly suitable for administration by subcutaneous injection compared to other compounds of generally comparable biological efficacy that are short-acting.

The peptide is hereinafter referred to as Peptide No. 1 and is assayed in vivo to determine its effectiveness to suppress secretion of LH in rats. Measurement of circulating LH levels in castrated male Sprague-Dawley rats treated subcutaneously with the peptide is carried out as reported in C. Rivier et al. *Biol. Reproduc.*, 1983. 29, 374–378. The peptides are first dissolved at a concentration of 1.0 or 10 mg/ml in bacteriostatic water and then further diluted in 0.04M phosphate buffer containing 0.1% BSA. Subsequent dilutions are made in phosphate buffer. The peptides are injected sc, and blood samples (300 μl) are collected under metotane anesthesia. Sera (50 ∥l) are tested for LH levels in duplicate using reagents provided by the National Pituitary and Hormone Distribution Program of the NIDDK. Testing shows that a dosage of 50 μg of peptide per rat suppresses LH secretion to levels that are less than 50% of control levels for the first 3 days, which levels are about the same as the LH levels exhibited by rats similarly injected with a dose of 50 micrograms of Acyline. However, 96 hours following injection, the LH levels are only about 75% of those of the Acyline-injected rats. Examination of the rats shows that the peptide was very well tolerated, with no significant gelling at the point of injection being detectable.

Experience gained from the testing of a large number of GnRH antagonists shows that a peptide exhibiting such long-acting suppression of LH would, if assayed in vivo in mature female Sprague-Dawley rats, fully block ovulation at a dosage of 2.5 micrograms.

EXAMPLE 2

A portion of the peptidoresin intermediate synthesized in Example 1 is used to create [D-Dpr(Cbm)$^3$]-Acyline. After removal of the Fmoc protecting group from the side chain of the D-Dpr residue as in Example 1, the intermediate is treated with t-butyl isocyanate for about 6 hours at room temperature. Cleavage from the resin and deprotection, followed by purification, are carried out as described in Example 1, which results in removal of the t-butyl, leaving the carbamoyl group substituted upon the amino side chain of the D-Dpr residue. The peptide Ac-β-D-2Nal-D-4Cpa-D-Dpr(carbamoyl)-Ser-4Aph(acetyl)-D-4Aph(acetyl)-Leu-Lys(isopropyl)-Pro-D-Ala-NH$_2$ (Peptide No. 2) is obtained in the RP-HPLC purification. It is judged to be homogeneous, and its purity is estimated to be greater than 98 percent. MS analysis shows a mass of 1513.7 Da, which is in agreement with the calculated mass of 1513.7 Da. From the HPLC results, it can be seen that this peptide is more hydrophilic than Peptide No. 1.

Assaying this peptide in the standard in vivo rat test as in Example 1, shows that, at a dosage of 50 micrograms, the peptide is bioactive, being about as effective for the suppression of LH as Peptide No. 1.

EXAMPLE 2A

A portion of the peptidoresin intermediate prepared in the synthesis set forth in Example 1 is utilized herein to form [D-Dpr(EtCbm)$^3$]-Acyline. After removal of the Fmoc protecting group from the side chain of the D-Dpr residue as in Example 1, the intermediate is treated with ethyl isocyanate for about 60 minutes at room temperature in the presence of DIEA to form an ethylurea group with the amino side chain of the D-Dpr residue. Cleavage from the resin and deprotection, followed by purification, are carried out as described in Example 1. The peptide Ac-β-D-2Nal-D-4Cpa-D-Dpr(ethylcarbamoyl)-Ser-4Aph(acetyl)-D-4Aph(acetyl)-Leu-Lys(isopropyl)-Pro-D-Ala-NH$_2$ is obtained in the RP-HPLC purification. It is judged to be homogeneous, and its purity is estimated to be greater than 98 percent. MS analysis shows a mass of 1541.4 Da, which is in agreement with the calculated mass of 1541.8 Da. From the HPLC results, it can be seen that this peptide is about as hydrophilic as Acyline.

Assaying this peptide in the standard in vivo rat test as in Example 1, shows that, at a dosage of 50 micrograms, the peptide is bioactive, being about as effective as Peptide No. 2 for the suppression of LH.

EXAMPLE 2B

Another portion of the peptidoresin intermediate prepared in Example 1 is utilized to form the decapeptide [D-Dpr(iprCbm)$^3$]-Acyline. After removal of the Fmoc protecting group from the side chain of the D-Dpr residue as in Example 1, the intermediate is treated with isopropylisocyanate for about 30 minutes at room temperature in the presence of DIEA to form an isopropylurea group with the amino side chain of the D-Dpr residue. Cleavage from the resin and deprotection, followed by purification, are carried out as described in Example 1. The peptide Ac-β-D-2Nal-D-4Cpa-D-Dpr(isopropylcarbamoyl)-Ser-4Aph(acetyl)-D-4Aph(acetyl)-Leu-Lys(isopropyl)-Pro-D-Ala-NH$_2$ is obtained in the RP-HPLC purification. It is judged to be homogeneous, and its purity is estimated to be greater than 95 percent. MS analysis shows a mass of 1555.5 Da, which is in agreement with the calculated mass of 1555.8 Da.

Assaying this peptide in the standard in vivo rat test as in Example 1, shows that, at a dosage of 50 micrograms, the peptide is bioactive, being about as effective an Acyline for 2 days. At 3 days, it is less effective than Acyline for the suppression of LH.

EXAMPLE 2C

The synthesis set forth in Example 1 is generally used to form a decapeptide intermediate wherein the D-Dpr, 4Aph and D-4Aph residues all remain protected by Fmoc. After acetylation of the N-terminus and then removal of the Fmoc protecting groups from the three side chains as in Example 1, the intermediate is treated with methyl isocyanate for about 2 hours at room temperature in the presence of DIEA to form methylurea groups with the three amino side chains. Cleavage from the resin and deprotection, followed by purification, are carried out as described in Example 1. The peptide Ac-β-D-2Nal-D-4Cpa-D-Dpr(methylcarbamoyl)-Ser-4Aph(methylcarbamoyl)-D-4Aph(methylcarbamoyl)-Leu-Lys(isopropyl)-Pro-D-Ala-NH$_2$ is obtained in the RP-HPLC purification. It is judged to be homogeneous and to be more hydrophilic than Acyline.

Assaying this peptide in the standard in vivo rat test as in Example 1, shows that, at a dosage of 50 micrograms, the peptide is bioactive, and about as effective as Acyline for the suppression of LH.

EXAMPLE 3

An analog of the peptide Cetrorelix having the formula Ac-D-2Nal-D-4Cpa-D-Dpr(methylcarbamoyl)-Ser-Tyr-D-Cit-Leu-Arg-Pro-D-Ala-NH$_2$ is synthesized using the synthesis as generally set forth in Example 1. Instead of coupling N$^\alpha$Boc-D-4Aph and 4Aph in the 6- and 5-positions, N$^\alpha$Boc-D-Cit is coupled in the 6-position, and N$^\alpha$Boc-Tyr(2BrZ) is coupled in the 5-position. N$^\alpha$Boc-Arg (Tos) is used instead of N$^\alpha$Boc-Lys(Ipr,Z) for the 8-position residue. Alternatively, N$^\alpha$Boc-D-Orn(Fmoc) is coupled in the 6-position, and the chain elongation is temporarily halted following the addition of Boc-Tyr(2BrZ) in the 5-position, having obtained the following peptide intermediate: Boc-Tyr(2BrZ)-D-Orn(Fmoc)-Leu-Arg(Tos)-Pro-D-Ala-NH-[MBHA resin support]. The amino side chain on the Orn residue is then deprotected by removal of the Fmoc protection as in Example 1, and the intermediate is treated with excess t-butyl isocyanate in DMF for about 6 hours at room temperature to react with the side chain of the Orn residue. The completion of the synthesis of the decapeptide intermediate is then carried out as in Example 1, followed by deprotection of the D-Dpr side chain and reaction with methyl isocyanate.

The peptidoresin is then subjected to the standard wash, and cleavage from the resin and deprotection, followed by purification, are carried out as described in Example 1. The peptide Ac-D-2Nal-D-4Cpa-D-Dpr(methylcarbamoyl)-Ser-Tyr-D-Cit-Leu-Arg-Pro-D-Ala-NH$_2$ (Peptide No. 3) is obtained following RP-HPLC purification. The peptide is considered to be more hydrophilic than Acyline and to have longer duration of in vivo suppression of LH than Cetrorelix.

EXAMPLE 3A

The synthesis set forth in Example 3 is repeated, substituting N$^\alpha$Boc-D-Hci for N$^\alpha$Boc-D-Cit and ILys$^8$ for Arg$^8$ to synthesize an analog of the decapeptide Antarelix. Following deprotection of the D-Dpr side chain, reaction is carried out with methyl isocyanate. Cleavage from the resin and deprotection, followed by purification, are carried out as described in Example 1. The peptide Ac-β-D-2Nal-D-4Cpa-D-Dpr(methylcarbamoyl)-Ser-Tyr-D-Hci-Leu-ILys-Pro-D-Ala-NH$_2$ is obtained in the RP-HPLC purification.

This peptide has substantially the same ability to suppress the in vivo secretion of LH as does Peptide No. 3.

EXAMPLE 4

An analog of the peptide Antide having the formula Ac-D-2Nal-D-4Cpa-D-Dpr(methylcarbamoyl)-Ser-Lys(nicotinoyl)-D-Lys(nicotinoyl)-Leu-Lys(ipr)-Pro-D-Ala-NH$_2$ is synthesized using the synthesis as generally set forth in Example 1 of U.S. Pat. No. 5,169,935, but substituting N$^\alpha$Boc-D-Dpr(Fmoc) for D-3Pal. Following the completion of the synthesis of the decapeptide intermediate, deprotection of the D-Dpr side chain and reaction with methyl isocyanate are carried out as in Example 1.

The peptidoresin is then subjected to the standard wash; then cleavage from the resin and deprotection, followed by purification, are carried out as described in Example 1. The peptide Ac-D-2Nal-D-4Cpa-D-Dpr(methylcarbamoyl)-Ser-Lys(Nic)-D-Lys(Nic)-Leu-ILys-Pro-D-Ala-NH$_2$ (Peptide No. 4) is obtained in the RP-HPLC purification. The peptide exhibits longer duration of in vivo suppression of LH secretion than Antide.

EXAMPLE 5

An analog of the peptide Azaline B having the formula Ac-D-2Nal-D-4Cpa-D-Dpr(methylcarbamoyl)-Ser-4Aph(atz)-D-4Aph(atz)-Leu-ILys-Pro-D-Ala-NH$_2$ is synthesized using the synthesis as generally set forth in Example VIII of U.S. Pat. No. 5,269,468. Instead of coupling N$^\alpha$Boc-D-3Pal in the 3-position, N$^\alpha$Boc-D-Dpr(Fmoc) is coupled in the 3-position. Following the completion of the synthesis of the decapeptide intermediate, deprotection of the D-Dpr side chain and reaction with methyl isocyanate are carried out as in Example 1.

The peptidoresin is then subjected to the standard wash, and cleavage from the resin and deprotection, followed by purification, are carried out as described in Example 1. The peptide Ac-D-2Nal-D-4Cpa-D-Dpr(methylcarbamoyl)-Ser-4Aph(atz)-D-4Aph(atz)-Leu-ILys-Pro-D-Ala-NH$_2$ (Peptide No. 5) is obtained in the RP-HPLC purification. This peptide is more hydrophilic than Acyline and exhibits longer duration of in vivo suppression of LH secretion than Azaline B.

EXAMPLE 5A

An analog of the peptide Antide, [D-Dpr(methylcarbamoyl)$^3$, 4Aph(Gab)(atz)$^5$, D-4Aph(Gab)(atz)$^6$]-Antide is synthesized using the synthesis as generally set forth in Example 1. After coupling N$^\alpha$Boc-D-4Aph(Fmoc) and N$^\alpha$Boc-4Aph(Fmoc) in the 6- and 5-positions, the chain elongation is temporarily halted and reaction with side chain-protected gamma-amino butyric acid (Gab) is carried out followed by the building of the triazole modifications as taught in Example 1 of U.S. Pat. No. 5,506,207. Following the completion of the synthesis of the decapeptide intermediate, deprotection of the D-Dpr side chain and reaction with methyl isocyanate are carried out as in Example 1.

The peptidoresin is then subjected to the standard wash, and cleavage from the resin and deprotection, followed by purification, are carried out as described in Example 1. The peptide Ac-D-2Nal-D-4Cpa-D-Dpr(methylcarbamoyl)-Ser-4Aph(Gab)(atz)-D-4Aph(Gab)(atz)-Leu-ILys-Pro-D-Ala-NH$_2$ (Peptide No. 5A) is obtained in the RP-HPLC purification. This peptide is more hydrophilic than Antide and exhibits longer duration of in vivo suppression of LH secretion than Acyline.

EXAMPLE 5B

Another analog of the peptide Antide [D-Dpr(methylcarbamoyl)$^3$, 4Aph(β-Ala)(atz)$^5$, D-4Aph(β-Ala)(atz)$^6$]-Antide is synthesized using the synthesis as generally set forth in Example 5A. Instead of reacting the side chain amino groups of D-4Aph and 4Aph in the 6- and 5-positions with Gab, the initial reaction is carried out with N$^\beta$Fmoc-β-Ala. The remainder of the synthesis is the same. Following the completion of the synthesis of the decapeptide intermediate, deprotection of the D-Dpr side chain and reaction with methyl isocyanate are carried out as in Example 1.

The peptidoresin is then subjected to the standard wash, and cleavage from the resin and deprotection, followed by purification, are carried out as described in Example 1. The peptide Ac-D-2Nal-D-4Cpa-D-Dpr(methylcarbamoyl)-Ser-4Aph(β-Ala)(atz)-D-4Aph(β-Ala)(atz)-Leu-ILys-Pro-D-Ala-NH$_2$ (Peptide No. 5B) is obtained in the RP-HPLC purification. This peptide is more hydrophilic than Antide and exhibits longer duration of in vivo suppression of LH secretion than Antide.

EXAMPLE 5C

Another analog of the peptide Antide, [D-Dpr(methylcarbamoyl)$^3$, 4Aph(For)$^5$, D-4Aph(For)$^6$]-Antide is synthesized using the synthesis as generally set forth in Example 1. Instead of reacting the side chain amino groups of D-4Aph and 4Aph in the 6- and 5-positions with acetic anhydride, the reaction is carried out with a mixture of formic acid and acetic anhydride. Following the completion of the synthesis of the decapeptide intermediate, deprotection of the D-Dpr side chain and reaction with methyl isocyanate are carried out as in Example 1.

The peptidoresin is then subjected to the standard wash, and cleavage from the resin and deprotection, followed by purification, are carried out as described in Example 1. The peptide Ac-D-2Nal-D-4Cpa-D-Dpr(methylcarbamoyl)-Ser-4Aph(For)-D-4Aph(For)-Leu-ILys-Pro-D-Ala-NH$_2$ (Peptide No. 5C) is obtained in the RP-HPLC purification. The peptide exhibits longer duration of in vivo suppression of LH secretion than Antide.

EXAMPLE 5D

The analog [D-Dpr(MeCbm)$^3$, 4Aph(Hor)$^5$]-Acyline is synthesized as generally set forth in Example 1. The 6-position D-4Aph is acetylated prior to the addition to the chain of N$^\alpha$Boc-4Aph(Fmoc). Following deprotection of the 4Aph side chain, a reaction is carried out with hydroorotic acid (C$_4$N$_2$H$_5$(O)$_2$COOH) in the presence of DIC and HOBt in DMF for about 8 hours at room temperature. Completion of the synthesis, cleavage from the resin and deprotection, followed by purification, are then carried out as described in Example 1. The peptide Ac-β-D-2Nal-D-4Cpa-D-Dpr(MeCbm)-Ser-4Aph(Hor)-D-4Aph(acetyl)-Leu-Lys(isopropyl)-Pro-D-Ala-NH$_2$ is obtained in the RP-HPLC purification and judged to be homogeneous, with its purity estimated to be greater than 99 percent. MS analysis shows a mass of 1625.5 Da which compares favorably to the expected mass of 1625.8 Da. From the HPLC results, it can be seen that this peptide is more hydrophilic than Acyline.

Assaying this peptide in the standard in vivo rat LH Suppression test shows that, at a dosage of 50 micrograms, it is substantially as active as Acyline in suppressing LH level for 2 days, and at 3 days it shows suppression of LH to levels less than Acyline.

EXAMPLE 5E

The analog [D-Dpr(MeCbm)$^3$, 4Aph(Hor)$^5$, D-Aph(Hor)$^6$]-Acyline is synthesized as generally set forth in Example 5D. The 6-position D-4Aph and the 5-position 4Aph residues are reacted simultaneously. Following deprotection of the two 4Aph side chains, the reaction is carried out with hydroorotic acid, and completion of the synthesis, cleavage from the resin and deprotection, and purification are then carried out as in Example 5D. The peptide Ac-β-D-2Nal-D-4Cpa-D-Dpr(methylcarbamoyl)-Ser-4Aph(Hor)-D-Aph(Hor)-Leu-Lys(isopropyl)-Pro-D-Ala-NH$_2$ is obtained in the RP-HPLC purification and judged to be homogeneous, with its purity estimated to be greater than 95 percent. MS analysis shows a mass of 1735.5 Da which compares favorably to the expected mass of 1735.8 Da. From the HPLC results, it can be seen that this peptide is more hydrophilic than Acyline.

Assaying this peptide in the standard in vivo rat LH Suppression test shows that, at a dosage of 50 micrograms, it is substantially as active as Acyline in suppressing LH level at 1, 2 and 3 days, and is considered to be long-acting.

EXAMPLE 5F

The analog [D-Dbu(MeCbm)$^3$, 4Aph(Hor)$^5$]-Acyline is synthesized as generally set forth in Example 5D, substituting N$^\alpha$Boc-D-Dbu(Fmoc) for N$^\alpha$Boc-D-Dpr(Fmoc). Completion of the synthesis, cleavage from the resin and deprotection, followed by purification, are then carried out as described in Example 1. The peptide Ac-β-D-2Nal-D-4Cpa-D-Dbu(MeCbm)-Ser-4Aph(Hor)-D-4Aph(acetyl)-Leu-Lys(isopropyl)-Pro-D-Ala-NH$_2$ is obtained in the RP-HPLC purification. The compound is bioactive in suppressing the secretion of LH.

EXAMPLE 6

The synthesis set forth in Example 1 is repeated to form the peptide [D-Dpr(MeCbm)$^3$, 4Aph(Cbm) 5, D-4Aph(Cbm)$^6$]-Antide. Instead of reacting the side chain amino groups of 4Aph and D-4Aph with acetic anhydride, they are both reacted with t-butyl isocyanate; removal of Boc to permit further extension of the peptide chain result in removal of the t-butyl moieties. Following acetylation of the N-terminus and then deprotection of the D-Dpr side chain, reaction with methyl isocyanate is carried out. Cleavage from the resin and deprotection, followed by purification, are carried out as described in Example 1 and results in the removal of any t-butyl moieties. The peptide Ac-β-D-2Nal-D-4Cpa-D-Dpr(methylcarbamoyl)-Ser-4Aph(carbamoyl)-D-4Aph(carbamoyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1529.9 Da which compares favorably to the expected mass of 1529.8 Da. From the HPLC results, it can be seen that this peptide is more hydrophilic than Acyline.

Assaying this peptide in the standard in vivo rat LH Suppression test shows that, at a dosage of 50 micrograms, it is substantially as long acting as Acyline.

EXAMPLE 7

The peptide analog [D-Gln$^3$]-Acyline is synthesized using the synthesis as generally set forth in Example 1. Instead of coupling N$^\alpha$Boc-D-Dpr(Fmoc) in the 3-position, N$^\alpha$Boc-D-Gln is used. Optionally, N$^\alpha$Boc-D-Gln(Xan) is used; however, preferably D-Gln is coupled without side chain protection. Following the completion of the synthesis of the decapeptide intermediate, the peptidoresin is subjected to the standard wash; then, cleavage from the resin and deprotection, followed by purification, are carried out as described in Example 1. The peptide Ac-D-2Nal-D-4Cpa-D-Gln-Ser-4Aph(Ac)-D-4Aph(Ac)-Leu-ILys-Pro-D-Ala-NH$_2$ (Peptide No. 7) is obtained in the RP-HPLC purification. It is judged to be homogeneous, and its purity is estimated to be greater than 99 percent. LSIMS analysis shows measured mass of 1512.9 Da which is in agreement with the calculated mass of 1512.7 Da for this peptide. When tested in vivo for suppression of LH secretion as in Example 1, the peptide exhibits about the same duration of bioactivity as Acyline over 3 days.

EXAMPLE 7A

The analog [D-Gln$^3$, 4Aph(Hor)$^5$]-Acyline is synthesized as generally set forth in Examples 5D and 7. The 6-position D-4Aph is acetylated prior to the addition to the chain of N$^\alpha$Boc-4Aph(Fmoc). Following deprotection of the 4Aph side chain, a reaction is carried out with hydroorotic acid as in Example 5D. Following completion of the synthesis and purification, the peptide Ac-β-D-2Nal-D-4Cpa-D-Gln-Ser-4Aph(Hor)-D-4Aph(acetyl)-Leu-Lys(isopropyl)-Pro-D-Ala-NH$_2$ is obtained in the RP-HPLC purification and judged to be homogeneous, with its purity estimated to be greater than 95 percent. MS analysis shows a mass of 1610.9 Da which compares favorably to the expected mass of 1610.8 Da. From the HPLC results, it can be seen that this peptide is more hydrophilic than Acyline.

Assaying this peptide in the standard in vivo rat LH Suppression test shows that, at a dosage of 50 micrograms, it is substantially as active as Acyline in suppressing LH level at 1, 2 and 3 days, and at 96 hours it shows suppression of LH to levels well below Acyline. It is considered to be very long-acting.

EXAMPLE 7B

The synthesis set forth in Example 7A is repeated to create a peptide which substitutes D-Gln(Me)$^3$ for D-Gln$^3$. A simple substitution of N$^\alpha$Boc-D-Gln(Me) for N$^\alpha$Boc-D-Gln may be used. Alternatively, following addition of Boc-D-Glu(OFm) and the removal of the fluorenylmethyl ester side chain protecting group, a reaction is carried out with NH$_2$CH$_3$.HCl in the presence of DIEA and BOP (benzotriazoyl-N-oxytris(dimethylamino) phosphonium hexafluorophosphate) to form the N-methylamide. Cleavage from the resin and deprotection, followed by purification, are carried out as described in Example 1. The peptide Ac-β-D-2Nal-D-4Cpa-D-Gln(methyl)-Ser-4Aph(hydroorotyl)-D-4Aph(acetyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1624.8 Da which compares favorably to the expected mass of 1624.8 Da. From the HPLC results, it can be seen that this peptide is more hydrophilic than Acyline.

Assaying this peptide in the standard in vivo rat LH Suppression test shows that, at a dosage of 50 micrograms, it is substantially as long acting as Acyline for 3 days and remains somewhat less effective through day 4.

EXAMPLE 7C

The synthesis set forth in Example 7A is repeated, substituting N$^\alpha$Boc-D-4Amf(Fmoc) for N$^\alpha$Boc-D-4Aph(Fmoc) and then reacting its deprotected side chain with t-butyl isocyanate prior to the addition of N$^\alpha$Boc-4Aph(Fmoc). The peptide Ac-β-D-2Nal-D-4Cpa-D-Gln-Ser-4Aph(hydroorotyl)-D-4Amf(carbamoyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1625.8 Da which compares favorably to the expected mass of 1625.8 Da. From the HPLC results, it can be seen that this peptide is more hydrophilic than Acyline.

Assaying this peptide in the standard in vivo rat LH suppression test shows that, at a dosage of 50 micrograms, it is substantially as effective as Acyline for 2 to 3 days.

EXAMPLE 7D

The synthesis of Example 7C is generally followed to make [N-MeCbm-D-2Nal$^1$, D-Gln$^3$, 4Aph(Hor)$^5$, D-4Amf(Cbm)$^6$]-Antide; however, Fmoc protection is not removed from 4Aph until after the reaction at the N-terminus. Following deprotection of the N-terminus, a reaction is carried out with methyl isocyanate. Then, Fmoc is removed and 4Aph is reacted with hydroorotic acid as in Example 7A. Cleavage from the resin and deprotection, followed by purification, are then carried out as described in Example 1. The peptide N-methylcarbamoyl-β-D-2Nal-D-4Cpa-D-Gln-Ser-4Aph(hydroorotyl)-D-4Amf(carbamoyl)-Leu-Lys(isopropyl)-Pro-D-Ala-NH$_2$ is obtained in the RP-HPLC purification and judged to be homogeneous, with its purity estimated to be greater than 99 percent. MS analysis shows a mass of 1640.8 Da which compares favorably to the expected mass of 1640.8 Da. From the HPLC results, it can be seen that this peptide is more hydrophilic than Acyline.

Assaying this peptide in the standard in vivo rat LH suppression test shows that, at a dosage of 50 micrograms, it is substantially as effective as Acyline for 2 to 3 days.

EXAMPLE 7E

The synthesis set forth in Example 7C is repeated, substituting methyl isocyanate for t-butyl isocyanate in carrying out the reaction with the deprotected side chain of D-4Amf. Cleavage from the resin and deprotection, followed by purification, are subsequently carried out as described in Example 1. The peptide Ac-β-D-2Nal-D-4Cpa-D-Gln-Ser-4Aph(hydroorotyl)-D-4Amf(methylcarbamoyl)-Leu-Lys(isopropyl)-Pro-D-Ala-NH$_2$ is obtained in the RP-HPLC purification and judged to be homogeneous, with its purity estimated to be greater than 99 percent. MS analysis shows a mass of 1639.7 Da which compares favorably to the expected mass of 1639.8 Da. From the HPLC results, it can be seen that this peptide is more hydrophilic than Acyline.

Assaying this peptide in the standard in vivo rat LH suppression test shows that, at a dosage of 50 micrograms, it is substantially as effective as Acyline for 2 to 3 days.

EXAMPLE 7F

The synthesis set forth in Example 7C is repeated, substituting N$^\alpha$Boc-4Amf(Fmoc) for N$^\alpha$Boc-4Aph(Fmoc) to create the analog of [D-Gln$^3$, 4Amf(Hor)$^5$, D-4Amf(Cbm)$^6$]-Antide. Cleavage from the resin and deprotection, followed by purification, are subsequently carried out as described in Example 1. The peptide Ac-β-D-2Nal-D-4Cpa-D-Gln-Ser-4Amf(hydroorotyl)-D-4Amf(carbamoyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1639.7 Da which compares favorably to the expected mass of 1639.8 Da. From the HPLC results, it can be seen that this peptide is more hydrophilic than Acyline.

Assaying this peptide in the standard in vivo rat LH suppression test shows that, at a dosage of 50 micrograms, it remains effective and is slightly better than Acyline after 4 days.

EXAMPLE 7G

The synthesis set forth in Example 7D is repeated, substituting D-hydroorotic acid for L-hydroorotic acid in the reaction with the deprotected side chain of 4Aph to create the analog [N-MeCbm-D-2Nal$^1$, D-Gln$^3$, 4Aph(D-Hor)$^5$, D-4Amf(Cbm)$^6$-Antide. Should the peptidoresin contain the hydroorotyl group when the reaction with an isocyanate is to take place, the base, e.g. DIEA, is not added and only 3 eq. of the particular isocyanate is employed. Cleavage from the resin and deprotection, followed by purification, are subsequently carried out as described in Example 1. The peptide N-methylcarbamoyl-β-D-2Nal-D-4Cpa-D-Gln-Ser-4Aph(D-hydroorotyl)-D-4Amf(carbamoyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1640.7 Da which compares favorably to the expected mass of 1640.8 Da. From the HPLC results, it can be seen that this peptide is more hydrophilic than Acyline.

Assaying this peptide in the standard in vivo rat LH suppression test shows that, at a dosage of 50 micrograms, it is short-acting, being nearly as effective as Acyline for 1 day and then fairly quickly losing its effectiveness.

EXAMPLE 7H

The synthesis set forth in Example 7D is repeated, substituting L-Imz for L-hydroorotic acid in the reaction with the deprotected side chain of 4Aph to create the analog [N-MeCbm-D-2Nal$^1$, D-Gln$^3$, 4Aph(Imz)$^5$, D-4Amf(Cbm)$^6$]-Antide. Cleavage from the resin and deprotection, followed by purification, are subsequently carried out as described in Example 1. The peptide N-methylcarbamoyl-β-D-2Nal-D-4Cpa-D-Gln-Ser-4Aph(Imz)-D-4Amf (carbamoyl)-Leu-Lys(isopropyl)-Pro-D-Ala-NH$_2$ is obtained in the RP-HPLC purification. This peptide is more hydrophilic than Acyline and is substantially as effective as Acyline for 2 to 3 days in LH suppression.

EXAMPLE 7I

The synthesis set forth in Example 7F is repeated, substituting methyl isocyanate for t-butyl isocyanate in carrying out the reaction with the deprotected side chain of D-4Amf to create the analog of [D-Gln$^3$, 4Amf(Hor)$^5$, D-4Amf(MeCbm)$^6$]-Antide. Cleavage from the resin and deprotection, followed by purification, are subsequently carried out as described in Example 1. The peptide Ac-β-D-2Nal-D-4Cpa-D-Gln-Ser-4Amf(hydroorotyl)-D-4Amf(methylcarbamoyl)-Leu-Lys(isopropyl)-Pro-D-Ala-NH$_2$ is obtained in the RP-HPLC purification and judged to be homogeneous, with its purity estimated to be greater than 98 percent. MS analysis shows a mass of 1653.7 Da which compares favorably to the expected mass of 1653.8 Da. From the HPLC results, it can be seen that this peptide is more hydrophilic than Acyline.

Assaying this peptide in the standard in vivo rat LH suppression test shows that, at a dosage of 50 micrograms, it is substantially as effective as Acyline for 3 days and remains effective through day 4.

EXAMPLE 7J

The synthesis set forth in Example 7A is repeated, substituting N$^\alpha$Boc-4Amf(Fmoc) for N$^\alpha$Boc-4Aph(Fmoc) to create the analog of [D-Gln$^3$, 4Amf(Hor)$^5$]-Acyline. The peptide Ac-β-D-2Nal-D-4Cpa-D-Gln-Ser-4Amf(hydroorotyl)-D-4Aph(acetyl)-Leu-Lys(isopropyl)-Pro-D-Ala-NH$_2$ is obtained in the RP-HPLC purification and judged to be homogeneous, with its purity estimated to be greater than 99 percent. MS analysis shows a mass of 1624.8 Da which compares favorably to the expected mass of 1624.8 Da. From the HPLC results, it can be seen that this peptide is more hydrophilic than Acyline.

Assaying this peptide in the standard in vivo rat LH suppression test shows that, at a dosage of 50 micrograms, it is nearly as effective as Acyline both after 3 days and after 4 days.

EXAMPLE 7K

The analog [D-Asn$^3$, 4Aph(Hor)$^5$]-Acyline is synthesized as generally set forth in Example 7A, except that N$^\alpha$Boc-D-Asn is used instead of N$^\alpha$Boc-D-Gln. The peptide Ac-β-D-2Nal-D-4Cpa-D-Asn-Ser-4Aph(Hor)-D-Aph(acetyl)-Leu-Lys(isopropyl)-Pro-D-Ala-NH$_2$ is obtained in the RP-HPLC purification and judged to be homogenous, with its purity estimated to be about 99 percent. MS analysis shows a mass of 1596.9 Da which compares favorably to the expected mass of 1596.7 Da. From the HPLC results, it can be seen that this peptide is more hydrophilic than Acyline.

Assaying this peptide in the standard in vivo rat LH Suppression test shows that, at a dosage of 50 micrograms, it is substantially as active as Acyline in suppressing LH level for 2 days, and at 3 days it shows suppression of LH to levels less than Acyline.

EXAMPLE 8

The peptide [Gln$^3$]-Acyline is synthesized by repeating the synthesis set forth in Example 7 but coupling N$^\alpha$Boc-Gln in the 3-position instead of N$^\alpha$Boc-D-Gln. The peptide Ac-D-2Nal-D-4Cpa-Gln-Ser-4Aph(Ac)-D-4Aph(Ac)-Leu-ILys-Pro-D-Ala-NH$_2$ (Peptide No. 8) is obtained in the RP-HPLC purification. It is judged to be homogeneous, and its purity is estimated to be greater than 99 percent. LSIMS analysis shows measured mass of 1512.7 Da which is in agreement with the calculated mass of 1512.7 Da for this peptide. The peptide exhibits about the same duration of bioactivity as Acyline when tested in vivo for suppression of LH secretion as in Example 1, being about equal to Acyline over 4 days. It is considered to be long-acting.

EXAMPLE 8A

The analog [Gln$^3$, 4Aph(Hor)$^5$]-Acyline is synthesized as set forth in Example 7A, substituting N$^\alpha$Boc-Gln for N$^\alpha$Boc-D-Gln. The peptide Ac-β-D-2Nal-D-4Cpa-Gln-Ser-4Aph(Hor)-D-Aph(acetyl)-Leu-Lys(isopropyl)-Pro-D-Ala-NH$_2$ is obtained in the RP-HPLC purification and judged to be homogeneous, with its purity estimated to be about 99 percent. MS analysis shows a mass of 1610.7 Da which compares favorably to the calculated mass of 1610.8 Da. From the HPLC results, it can be seen that this peptide is more hydrophilic than Acyline.

Assaying this peptide in the standard in vivo rat LH Suppression test shows that, at a dosage of 50 micrograms, it is substantially as active as Acyline in suppressing LH levels over 4 days. It is considered to be long-acting.

EXAMPLE 8B

The synthesis set forth in Example 8A is repeated to create a peptide which substitutes Gln(Me)$^3$ for D-Gln$^3$. A simple substitution of N$^\alpha$Boc-Gln(Me) for N$^\alpha$Boc-Gln is used. The peptide Ac-β-D-2Nal-D-4Cpa-Gln(methyl)-Ser-4Aph(hydroorotyl)-D-4Aph(acetyl)-Leu-Lys(isopropyl)-Pro-D-Ala-NH$_2$ is obtained in the RP-HPLC purification. This peptide is more hydrophilic than Acyline. At a dosage of 50 micrograms, it is substantially as long acting as Acyline.

EXAMPLE 8C

The synthesis set forth in Example 8A is repeated, substituting N$^\alpha$Boc-D-4Amf(Fmoc) for N$^\alpha$Boc-D-4Aph(Fmoc) and then reacting its deprotected side chain with t-butyl isocyanate. The peptide Ac-β-D-2Nal-D-4Cpa-Gln-Ser-4Aph(hydroorotyl)-D-4Amf(carbamoyl)-Leu-Lys(isopropyl)-Pro-D-Ala-NH$_2$ is obtained in the RP-HPLC purification. This peptide is more hydrophilic than Acyline. It is judged to be homogeneous, and its purity is estimated to be greater than 99 percent. MS analysis shows a mass of 1625.6 Da, which is in agreement with the calculated mass of 1625.8 Da.

Assaying this peptide in the standard in vivo rat test as in Example 1, shows that, at a dosage of 50 micrograms, the peptide is bioactive, being about as effective as Acyline for 24 hours. At 2 days, it is somewhat less effective than Acyline for the suppression of LH and its effectiveness declines rapidly thereafter.

EXAMPLE 8D

The synthesis set forth in Example 8C is repeated, substituting methyl isocyanate for t-butyl isocyanate in carrying out the reaction with the deprotected side chain of D-4Amf. Cleavage from the resin and deprotection, followed by purification, are subsequently carried out as described in Example 1. The peptide Ac-β-D-2Nal-D-4Cpa-Gln-Ser-4Aph(hydroorotyl)-D-4Amf(methylcarbamoyl)-Leu-Lys(isopropyl)-Pro-D-Ala-NH$_2$ is obtained in the RP-HPLC purification. This peptide is more hydrophilic than Acyline. At a dosage of 50 micrograms, it is substantially as effective as Acyline for 2 to 3 days.

EXAMPLE 8E

The synthesis set forth in Example 8C is repeated, substituting N$^\alpha$Boc-4Amf(Fmoc) for N$^\alpha$Boc-4Aph(Fmoc) to create the analog of [Gln$^3$, 4Amf(Hor)$^5$, D-4Amf(Cbm)$^6$]-Antide. Cleavage from the resin and deprotection, followed by purification, are subsequently carried out as described in Example 1. The peptide Ac-β-D-2Nal-D-4Cpa-Gln-Ser-4Amf(hydroorotyl)-D-4Amf(carbamoyl)-Leu-Lys(isopropyl)-Pro-D-Ala-NH$_2$ is obtained in the RP-HPLC purification. This peptide is more hydrophilic than Acyline. At a dosage of 50 micrograms, it is about as effective as Acyline over 4 days.

EXAMPLE 8F

The synthesis set forth in Example 8E is repeated, substituting methyl isocyanate for t-butyl isocyanate in carrying out the reaction with the deprotected side chain of D-4Amf. Cleavage from the resin and deprotection, followed by purification, are subsequently carried out as described in Example 1. The peptide Ac-β-D-2Nal-D-4Cpa-Gln-Ser-4Aph(hydroorotyl)-D-4Amf(methylcarbamoyl)-Leu-Lys(isopropyl)-Pro-D-Ala-NH$_2$ is obtained in the RP-HPLC purification. This peptide is more hydrophilic than Acyline. At a dosage of 50 micrograms, it is substantially as effective as Acyline for 3 days.

EXAMPLE 8G

The synthesis set forth in Example 8A is repeated, substituting N$^\alpha$Boc-4Amf(Fmoc) for N$^\alpha$Boc-4Aph(Fmoc) to create the analog of [Gln$^3$, 4Amf(Hor)$^5$]-Acyline. Cleavage from the resin and deprotection, followed by purification, are subsequently carried out as described in Example 1. The peptide Ac-β-D-2Nal-D-4Cpa-Gln-Ser-4Amf(hydroorotyl)-D-4Aph(acetyl)-Leu-Lys(isopropyl)-Pro-D-Ala-NH$_2$ is obtained in the RP-HPLC purification. This peptide is more hydrophilic than Acyline. At a dosage of 50 micrograms, it is about as effective as Acyline over 3 days.

EXAMPLE 8H

The synthesis set forth in Example 8A is repeated to create a peptide which substitutes Asn$^3$ for D-Gln$^3$. A simple substitution of N$^\alpha$Boc-Asn for N$^\alpha$Boc-Gln is used. The peptide Ac-β-D-2Nal-D-4Cpa-Asn-Ser-4Aph(hydroorotyl)-D-4Aph(acetyl)-Leu-Lys(isopropyl)-Pro-D-Ala-NH$_2$ is obtained in the RP-HPLC purification. This peptide is more hydrophilic than Acyline. At a dosage of 50 micrograms, it is substantially as long acting as Acyline.

EXAMPLE 9

Using the procedures as generally set forth in Examples 1 to 7, the following GnRH antagonist peptides are also prepared:

[Acr-D-2Nal$^1$,4FD-Phe$^2$,D-Dpr(MeCbm)$^3$]-Acyline
[Bz-D-2Nal$^1$,4NO$_2$D-Phe$^2$,D-Dpr(MeCbm)$^3$,4Aph(Hor)$^5$]-Acyline
[For-D-2Nal$^1$,4OCH$_3$D-Phe$^2$,D-Dpr(MeCbm)$^3$,4Amf(Hor)$^5$]-Acyline
[Bz-D-2Nal$^1$,4BrD-Phe$^2$,D-Dpr(MeCbm)$^3$,D-4Aph(Imz)$^6$]-Acyline
[Pn-D-2Nal$^1$,4CH$_3$D-Phe$^2$,D-Dpr(MeCbm)$^3$,4Aph(MeCbm)$^5$]-Acyline
[Bt-D-2Nal$^1$,3,4Cl$_2$D-Phe$^2$,D-Dpr(MeCbm)$^3$,4Aph(Cbm)$^5$]-Acyline
[Vl-D-2Nal$^1$,4NO$_2$D-Phe$^2$,D-Gln$^3$,D-4Aph(Cbm)$^6$]-Acyline
[Vac-D-2Nal$^1$, C$^\alpha$Me4ClD-Phe$^2$, D-Gln$^3$,4Aph(Hor)$^5$]-Acyline
[Pn-D-2Nal$^1$,D-Gln$^3$,4Aph(Imz)$^5$,D-4Amf(Hor)$^6$,Agl$^{10}$]-Antide
[Acr-D-2Nal$^1$,D-Gln$^3$,4Ahp(Hor)$^5$,Arg$^8$,D-Agl(Me)$^{10}$]-Acyline
(MeCbm-D-2Nal$^1$,D-Gln$^3$,4Aph(Cbm)$^5$,Agl(Me)$^{10}$]-Acyline
[Cbm-D-2Nal$^1$,D-Dpr(MeCbm)$^3$,4Amf(MeCbm)$^5$,D-Agl$^{10}$]-Acyline
[EtCbm-D-2Nal$^1$,D-Dpr(MeCbm)$^3$,4Amf(iprcbm)$^5$, Pro$^9$NHCH$_2$CH$_3$]-Acyline
[Acr-D-2Nal$^1$,D-Gln$^3$,4Aph(Imz)$^5$,D-4Amf(Cbm)$^6$,Ala$^{10}$]-Antide
[Cbm-D-2Nal$^1$,D-Dpr(Cbm)$^3$,4Aph(MeCbm)$^5$,Arg(Et$_2$)$^8$]-Acyline
[D-Dpr(Cbm)$^3$,4Ahp(Hor)$^5$,D-4Ahp(Imz)$^6$,D-Agl$^{10}$]-Antide
[Ac-D-1Nal$^1$,D-Gln$^3$,4Amf(Hor)$^5$,D-4Amf(Hor)$^6$,Arg$^8$]-Antide
[PrCbm-D-2Nal$^1$,D-Gln$^3$,D-4Aph(EtCbm)$^6$, Pro$^9$NHCH$_2$CH$_3$]-Acyline
[D-Dpr(MeCbm)$^3$,4Amf(Hor)$^5$,AzaGly$^{10}$]-Antide
[D-Dpr(Cbm)$^3$,4Amf(Hor)$^5$,D-Cit$^6$,Har$^8$]-Acyline
[D-Dpr(EtCbm)$^3$,4Aph(Hor)$^5$,D-4Aph(D-Imz)$^6$,Gly$^{10}$]-Antide
[D-Dpr(Cbm)$^3$,D-Hci$^6$,Agl(Me)$^{10}$]-Antide
[D-Gln$^3$,4Aph(Hor)$^5$,D-3Pal$^6$,Har$^8$,Ala$^{10}$]-Antide
[D-Dpr(Cbm)$^3$,4Aph(Hor)$^5$,D-4Aph(For)$^6$,D-Agl(Me)$^{10}$]-Antide
[D-Dpr(EtCbm)$^3$,4Aph(Hor)$^5$,D-4Aph(atz)6,Har(Et$_2$)$^8$]-Antide
[D-Gln$^3$,4Aph(Hor)$^5$,D-4Aph(iprCbm)$^6$,D-Agl$^{10}$]-Antide
[For-D-1Nal$^1$,D-Dpr(EtCbm)$^3$,4Amf(Hor)$^5$,D-4Amf(atz)$^6$]-Antide These peptides are biopotent in inhibiting the secretion of LH.

EXAMPLE 10

Using the procedures as generally set forth in Examples 1 to 8, the following GnRH antagonist peptides are also prepared:

[For-D-2Nal$^1$,4CH$_3$D-Phe$^2$,Gln$^3$,4Amf(Hor)$^5$]-Acyline
[Bz-D-2Nal$^1$,4BrD-Phe$^2$,Gln$^3$,D-4Aph(Imz)$^6$]-Acyline
[Acr-D-2Nal$^1$,Gln$^3$,4Ahp(Hor)$^5$,Arg$^8$,D-Agl(Me)$^{10}$]-Acyline
[For-D-2Nal$^1$,4NO$_2$D-Phe$^2$,Gln$^3$,D-4Aph(Cbm)$^6$]-Acyline
[Bz-D-2Nal$^1$,C$^\alpha$Me4ClD-Phe$^2$,Gln$^3$,4Aph(Hor)$^5$]-Acyline
[Pn-D-2Nal$^1$,Gln$^3$,4Aph(Imz)$^5$,D-4Amf(Hor)$^6$,Agl$^{10}$]-Antide
[MeCbm-D-2Nal$^1$,Gln$^3$,4Aph(Cbm)$^5$,Agl(Me)$^{10}$]-Acyline
[PrCbm-D-2Nal$^1$,Gln$^3$,D-4Aph(EtCbm)$^6$,Pro$^9$NHCH$_2$CH$_3$]-Acyline
[Gln$^3$,4Aph(Hor)$^5$,D-4Aph(iprCbm)$^6$,D-Agl$^{10}$]-Antide

[Gln³,4Aph(Hor)⁵,D-3Pal⁶,Har⁸,Ala¹⁰]-Antide
[Ac-D-1Nal¹,Gln³,4Amf(Hor)⁵,D-4Amf(Hor)⁶,Arg⁸]-Antide
[Gln³,4Amf(Hor)⁵,D-Cit⁶,Har⁸]-Acyline
[Gln³,4Aph(Hor)⁵,D-4Aph(atz)⁶,Har(Et₂)⁸]-Antide
[For-D-1Nal¹,Gln³,4Amf(Hor)⁵,D-4Amf(atz)⁶]-Antide
[Acr-D-2Nal¹,Gln³,4Aph(Imz)⁵,D-4Amf(Cbm)⁶,Ala¹⁰]-Antide These peptides are biopotent in inhibiting the secretion of LH.

The foregoing compounds which were tested were shown to exhibit biological potency, from the standpoint of suppression of LH, at least generally comparable to the corresponding GnRH antagonist peptide known as Acyline, of which each is an analog. As a result of extensive testing in this area for over a decade, biopotency determined in this widely accepted test constitutes evidence as to biopotency of such compounds to suppress gonadotropin secretion and thus to have anti-ovulatory and antigonadal effect. Based upon superior solubility, resistance to in vivo gelling, long duration of bioactivity and other properties, these compounds are considered to be generally useful to suppress the secretion of gonadotropins and inhibit the release of steroids by the gonads, e.g. as anti-ovulatory agents.

The compounds of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, pamoate, maleate, acetate, citrate, benzoate, succinate, alginate, malate, ascorbate, tartrate and the like; acetate and pamoate, the salt of pamoic acid, may be preferred. If the active ingredient is to be administered in tablet form, the tablet may contain a pharmaceutically-acceptable, nontoxic diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain an effective amount of the peptide in conjunction with a conventional, pharmaceutically-acceptable carrier or diluent. Usually, the dosage will be from about 10 micrograms to about 2.5 milligrams of the peptide per kilogram of the body weight of the host when given intravenously. The nature of these compounds may permit effective oral administration; however, oral dosages might be higher. Overall, treatment of subjects with these peptides is generally carried out in the same manner as the clinical treatment using other antagonists of GnRH, using a suitable carrier in which the compound is soluble and administering a dosage sufficient to suppress LH and FSH levels in the patient.

It may also be desirable to deliver the GnRH analog over prolonged periods of time, for example, for periods of one week to one year from a single administration, and slow release, depot or implant dosage forms may be utilized. For example, a suitable, slow-release depot formulation for injection may contain the GnRH antagonist or a salt thereof dispersed or encapsulated in a slow degrading, non-toxic or non-antigenic polymer such as a polylactic acid/polyglycolic acid polymer, for example, as described in U.S. Pat. No. 3,773,919. It is known to administer such slow-release dosage formulations by a poultice that may be applied within the mouth. These compounds may also be formulated into silastic implants.

These compounds can be administered to mammals intravenously, subcutaneously, intramuscularly, orally, percutaneously, e.g. intranasally or intravaginally generally to suppress the secretion of the gonadotropins, e.g. to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. An example of one typical dosage form is a bacteriostatic water solution at a pH of about 6 containing the peptide which solution is administered parenterally to provide an effective dose in the range of about 0.1 to about 2.5 mg/kg of body weight per day. These compounds are considered to be well-tolerated in vivo and to resist gelling; accordingly, they are considered to be particularly well-suited for administration by subcutaneous injection in a bacteriostatic water solution at appropriate concentrations, above about 0.75 mg/ml and even above about 1.0 mg/ml, without danger of gelling at the point of injection.

These GnRH antagonist peptides are also useful diagnostically, both in vivo and in vitro. These peptides can be injected in vivo followed by assaying the bloodstream of a patient to determine the extent of decrease of hormonal secretion, e.g. LH secretion. In vitro assays can be carried out to determine whether certain tumor cells are sensitive to GnRH. In such assays, tumor cell cultures are treated with the GnRH antagonist peptides and then monitored for hormonal secretions and cell proliferation.

Although the invention has been described with regard to its preferred embodiments, it should be understood that changes and modifications as would be obvious to one having the ordinary skill in this art may be made without departing from the scope of the invention which is set forth in the claims which are appended hereto. For example, alternatively in the synthesis, an isocyanate can be reacted with the amino side chain prior to coupling the α-amino protected amino acid into the peptide chain rather than modifying it while a part of the chain. Other substitutions known in the art which do not significantly detract from the effectiveness of the peptides may also be employed in the peptides of the invention. Whereas the N-terminus may be left unsubstituted or other equivalent acylating groups can be used, either acetyl or substituted or unsubstituted carbamoyl is preferred. Other substituted D-Phe, such as (4F) D-Phe, can be used in the 2-position. Instead of 4Aph(Ac), the aminoPhe group can be treated with alternative acylating agents as disclosed in U.S. Pat. No. 5,506,207, such as formic acid, β-Ala(atz) and gamma-aminobutyric acid(atz), which as indicated in the examples likewise result in GnRH antagonists that exhibit long-acting duration; thus, these are considered equivalents of D- and L-4Aph(Ac), respectively. Both Lys(Bu) and Lys(Et₂) are considered to be equivalents of ILys, as are Arg, Arg(Et₂), Har, and Har(Et₂); however, ILys is most preferred. Other hydrophobic amino acid residues can also be employed in the 1-position and in the 6-position (as mentioned hereinbefore), preferably in D-isomer form, and are considered equivalents of those specified. Moreover, the antagonists can be administered in the form of their pharmaceutically or veterinarially acceptable, nontoxic salts, as indicated hereinbefore, which are considered equivalents.

What is claimed is:

1. A linear GnRH antagonist peptide having the formula: X-D-2Nal-(A)D-Phe-Xaa$_3$-Ser-Xaa$_5$-Xaa$_6$-Leu-Xaa$_8$-Pro-Xaa$_{10}$ or a pharmaceutically acceptable salt thereof wherein:

X is an acyl group of 7 carbon atoms or less or Q, with Q being $$-\overset{O}{\underset{\|}{C}}-NHR,$$

with R being H or lower alkyl;

A is 4Cl, 4F, 4Br, 4NO$_2$, 4CH$_3$, 4OCH$_3$, 3,4Cl$_2$ or C$^\alpha$Me4Cl;

Xaa$_3$ is D-Gln, Gln, D-Asn, Asn or D-Dpr(Q);

Xaa$_5$ is Tyr, 4Aph(Q$_1$), 4Amf(Q$_1$), 4Ahp(Q$_1$) or Lys(Nic), with Q$_1$ being Q, For, Ac, 3-amino-1,2,4-triazole, β-Ala(3-amino-1,2,4-triazole) or Gab(3-amino-1,2,4-triazole);

Xaa$_6$ is D-4Aph(Q$_2$), D-4Amf(Q$_2$), D-4Ahp(Q$_2$), D-Lys(Nic), D-Cit, D-Hci or D-3Pal, with Q$_2$ being Q, For, Ac, 3-amino-1,2,4-triazole, β-Ala(3-amino-1,2,4-triazole) or Gab(3-amino-1,2,4-triazole);

Xaa$_8$ is Lys(ipr), Arg, Har, Har(Et$_2$), or Arg(Et$_2$); and

Xaa$_{10}$ is D-Ala-NH$_2$, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$.

2. A GnRH antagonist according to claim 1 wherein Xaa$_3$ is D-Dpr(Q).

3. A GnRH antagonist according to claim 2 wherein R is methyl.

4. A GnRH antagonist according to claim 2 wherein R is ethyl or H.

5. A GnRH antagonist according to claim 1 wherein X is Ac, Xaa$_8$ is Lys(ipr) and Xaa$_{10}$ is D-Ala-NH$_2$.

6. A GnRH antagonist according to claim 1 wherein Xaa$_3$ is D-Gln.

7. A GnRH antagonist according to claim 1 wherein Xaa$_3$ is Gln.

8. A GnRH antagonist according to claim 1 wherein Xaa$_5$ is 4Aph(Ac) and Xaa$_6$ is D-4Aph(Ac) or wherein Xaa$_5$ is 4Aph (3-amino-1,2,4-triazole) and Xaa$_6$ is D-4Aph(3-amino-1,2,4-triazole).

9. A GnRH antagonist according to claim 1 wherein Xaa$_5$ is Tyr and Xaa$_6$ is D-Cit; or Xaa$_5$ is Lys(Nic) and Xaa$_6$ is D-Lys(Nic); or Xaa$_5$ is Tyr and Xaa$_6$ is D-Hci.

10. A GnRH antagonist according to claim 1 having the formula: Ac-D-2Nal-D-4ClPhe-D-Dpr(methylCbm)-Ser-4Aph(Ac)-D-4Aph(Ac)-Leu-Lys(ipr)-Pro-D-Ala-NH$_2$.

11. A linear GnRH antagonist peptide having the formula: X-D-2Nal-D-4ClPhe-Xaa$_3$-Ser-Xaa$_5$-Xaa$_6$-Leu-Lys(ipr)-Pro-D-Ala-NH$_2$ or a pharmaceutically acceptable salt thereof wherein:

X is an acyl group of 7 carbon atoms or less or Q, with Q being $$-\overset{O}{\underset{\|}{C}}-NHR,$$

with R being H or methyl or ethyl;

Xaa$_3$ is D-Gln or Gln;

Xaa$_5$ is 4Aph(Ac), 4Aph(Q), 4Amf(Q), or 4Aph(3-amino-1,2,4-triazole); and

Xaa$_6$ is D-4Aph(Ac), D-4Amf(Q), D-4Aph(Q) or D-4Aph(3-amino-1,2,4-triazole).

12. A linear GnRH antagonist peptide having the formula: X-D-2Nal-(A)D-Phe-Xaa$_3$-Ser-Xaa$_5$-Xaa$_6$-Leu-Xaa$_8$-Pro-Xaa10 or a pharmaceutically acceptable salt thereof wherein:

X is For, Ac, Acr, Pn, Bt, Vl, Vac, Bz or Q, with Q being $$-\overset{O}{\underset{\|}{C}}-NHR,$$

and with R being H or methyl or ethyl;

A is 4Cl, 4F, 4Br, 4NO$_2$ 4CH$_3$, 4OCH$_3$, 3,4Cl$_2$ or C$^\alpha$Me4Cl;

Xaa$_3$ is D-Gln, Gln, D-Asn, Asn or D-Dpr(Q);

Xaa$_5$ is 4Aph(Q$_1$), 4Ahp(Q$_1$) or 4Amf(Q$_1$) with Q$_1$ being Ac, 3-amino-1,2,4-triazole, Q or (D— or L—Hor) or (D— or L—Imz)

Xaa$_6$ is D-4Aph(Q$_2$), D-4Amf(Q$_2$), D-Lys(Nic), D-Cit, D-Hci or D-3Pal, with Q$_2$ being For or Q$_1$;

Xaa$_8$ is Lys(ipr), Arg, Har, Har(Et$_2$) or Arg(Et$_2$); and

Xaa$_{10}$ is D-Ala-NH$_2$, NHCH$_2$CH$_3$, Gly-NH$_2$, AzaGly-NH$_2$, Ala-NH$_2$, Agl-NH$_2$, D-Agl-NH$_2$, Agl(Me)-NH$_2$ or D-Agl(Me)-NH$_2$.

13. A GnRH antagonist peptide according to claim 12 wherein Xaa$_3$ is D-Gln or Gln.

14. A GnRH antagonist according to claim 13 having the formula: Ac-D-2Nal-4ClD-Phe-Xaa$_3$-Ser-4Aph (hydroorotyl)-D-4Aph(Ac)-Leu-Lys(ipr)-Pro-D-Ala-NH$_2$, wherein Xaa$_3$ is D-Gln or Gln.

15. A GnRH antagonist according to claim 12 wherein Xaa$_3$is D-Dpr(Q) and R is methyl.

16. A GnRH antagonist according to claim 12 having the formula: Ac-D-2Nal-D-4ClPhe-D-Dpr(methylCbm)-Ser-4Aph (Cbm)-D-4Aph(Cbm)-Leu-Lys(ipr)-Pro-D-Ala-NH$_2$.

17. A pharmaceutical composition for inhibiting the secretion of gonadotropins in mammals comprising, as an active ingredient, an effective amount of a GnRH antagonist according to claim 12 in association with a nontoxic diluent.

18. A method for inhibiting the secretion of gonadotropins in mammals comprising administering an amount of a pharmaceutical composition according to claim 17 which effectively decreases LH and FSH levels.

19. A method for in vivo diagnosing of a condition where GnRH is causing hormonal secretion at greater than normal levels, which method comprises administering a GnRH antagonist peptide according to claim 12 and monitoring hormonal secretion levels.

20. A method for in vitro diagnosing of a condition wherein GnRH is causing tumor growth, which method comprises administering a GnRH antagonist peptide according to claim 12 to tumor cell cultures and monitoring said tumor cell cultures for tumor cell proliferation.

* * * * *

UNITED STATES PATENT AND TRADEMARK OFFICE
CERTIFICATE OF CORRECTION

PATENT NO. : 5,821,230
DATED : October 13, 1998
INVENTOR(S) : Jiang, et al.

It is certified that error appears in the above-identified patent and that said Letters Patent is hereby corrected as shown below:

Column 23, line 37, "4Aph(hydroorotyl)" should be --4Amf(hydroorotyl)--.

IN THE CLAIMS:

Column 28 (Claim 12), line 7, "Xaa10" should be --$Xaa_{10}$--.

Signed and Sealed this

Twenty-third Day of February, 1999

Attest:

Attesting Officer

Q. TODD DICKINSON

Acting Commissioner of Patents and Trademarks

UNITED STATES PATENT AND TRADEMARK OFFICE
Certificate

Patent No. 5,821,230

Patented: October 13, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Guangcheng Jiang, San Diego, CA; Graeme Semple, Hamphire, United Kingdom; and Jean E. F. Rivier, La Jolla, CA.

Signed and Sealed this Twenty-second Day of April 2003.

M. P. WOODWARD
*Supervisory Patent Examiner*
Art Unit 1631